United States Patent
Singh et al.

(10) Patent No.: US 9,890,229 B2
(45) Date of Patent: *Feb. 13, 2018

(54) PRECURSOR FOR CATALYST, PROCESS FOR PREPARING THE SAME AND ITS USE THEREOF

(71) Applicant: INDIAN OIL CORPORATION LIMITED, Mumbai (IN)

(72) Inventors: Gurmeet Singh, Faridabad (IN); Bhasker Bantu, Faridabad (IN); Sukhdeep Kaur, Faridabad (IN); Naresh Kumar, Faridabad (IN); Gurpreet Singh Kapur, Faridabad (IN); Shashi Kant, Faridabad (IN); Biswajit Basu, Faridabad (IN); Ravinder Kumar Malhotra, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 231 days.

This patent is subject to a terminal disclaimer.

(21) Appl. No.: 14/416,611

(22) PCT Filed: Sep. 24, 2013

(86) PCT No.: PCT/IB2013/058792
§ 371 (c)(1),
(2) Date: May 19, 2015

(87) PCT Pub. No.: WO2014/045259
PCT Pub. Date: Mar. 27, 2014

(65) Prior Publication Data
US 2015/0274857 A1    Oct. 1, 2015

(30) Foreign Application Priority Data
Sep. 24, 2012 (IN) .......................... 2649/MUM/2012

(51) Int. Cl.
C08F 110/06    (2006.01)
C07F 3/02      (2006.01)
C07F 7/00      (2006.01)

(52) U.S. Cl.
CPC .............. *C08F 110/06* (2013.01); *C07F 3/02* (2013.01); *C07F 7/006* (2013.01)

(58) Field of Classification Search
None
See application file for complete search history.

(56) References Cited

U.S. PATENT DOCUMENTS

| | | |
|---|---|---|
| 4,220,554 A | 1/1980 | Scatá et al. |
| 4,727,051 A | 2/1988 | Breen et al. |
| 4,792,640 A | 12/1988 | Mehta |
| 4,820,672 A | 4/1989 | Mehta |
| 4,820,879 A | 4/1989 | Mehta |
| 5,081,320 A | 1/1992 | Wang et al. |
| 5,108,972 A | 4/1992 | Wang et al. |
| 5,414,158 A | 5/1995 | Gurtzgen |
| 7,135,531 B2 | 11/2006 | Zhu et al. |
| 2009/0306315 A1 | 12/2009 | Ramjoie et al. |

FOREIGN PATENT DOCUMENTS

| | | |
|---|---|---|
| EP | 0 294 354 A2 | 12/1988 |
| EP | 0 926 165 A1 | 6/1999 |
| EP | 1273595 A1 | 1/2003 |
| EP | 1 403 292 A1 | 3/2004 |

*Primary Examiner* — Catherine S Branch
(74) *Attorney, Agent, or Firm* — Maschoff Brennan

(57) ABSTRACT

The present invention provides a liquid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.1-99.8:0.1-99.8:0.1-99.8, and a process for preparing the same. The said process comprises contacting a magnesium source with an organohalide and alcohol in a solvent to form the liquid organomagnesium precursor. The present invention also provides a catalyst system using the organomagnesium precursor and its use thereof for polymerization of olefins. An illustrative example of the claimed process to make the organomagnesium precursor is: At 25° C., magnesium (powder or turnings) is added to organohalide, followed by alcohol in toluene. After heating to 90° C. and keeping there for 6 h the solution became viscous.

27 Claims, No Drawings

PRECURSOR FOR CATALYST, PROCESS FOR PREPARING THE SAME AND ITS USE THEREOF

FIELD OF INVENTION

The present invention relates to a catalyst system. More particularly, the present invention relates to a liquid organomagnesium precursor for the catalyst system, process for preparing the same, and the catalyst system using the organomagnesium precursor and its use thereof for polymerization of olefins.

BACKGROUND OF THE INVENTION

Ziegler-Natta catalyst systems are well known for their capability to polymerize olefins. They in general consist of a support which mostly is magnesium based onto which titanium component has been added along with organic compound known as internal donor. This catalyst when combined with co-catalyst and/or external donor comprise of the complete ZN catalyst system.

Ziegler-Natta catalyst system which typically consists of transition metal halide normally titanium halide supported on metal compound which is typically magnesium dichloride. Along with transition metal, there is an organic component known as internal electron donor that plays a typical role during catalyst synthesis and polymerization. $MgCl_2$ carrier, where the $MgCl_2$ is in active form, can be created by various methodologies. One of the methods is precipitating the $MgCl_2$ from an organic solution where magnesium is present as a soluble compound. The soluble magnesium compound can be achieved by starting from a magnesium alkyl and treating it with an alcohol. This step is then followed by chlorination of Mg alkyl or alkoxy compounds by a chlorination agent. The magnesium carrier can also be precipitated in the form of 'ready-made' $MgCl_2$. In that case the $MgCl_2$ has to be dissolved first in some suitable donor compound and then precipitated in hydrocarbon solvent. The $MgCl_2$ support material can also be precipitated by chlorinating a soluble magnesium alkyl compound simply by treating it with chlorine gas or hydrochloric acid. Once the desired specification of carrier is obtained, this is generally followed by titanation procedure which finally results in the catalyst synthesis.

U.S. Pat. No. 4,220,554 of Montedison describes the process of synthesizing the catalyst by treating Ti compounds with a spherical carrier which consists of Mg compound having the formula $X_nMg(OR)_{2-n}$. $X_nMg(OR)_{2-n}$ is synthesized by in reacting, in a single step, Mg metal, the organic halide and the orthosilicic acid ester. This product is isolated and then treated with halide of aromatic acid which is again isolated and treated with Ti compound for formation of catalyst. This catalyst is evaluated for propylene polymerization. This route applies the usage of orthosilicic ester for generation of magnesium alkoxy halide compound and focuses on the particle shape as well as size of the catalyst.

U.S. Pat. No. 4,727,051 of Stauffer Chemical Company discloses the process for synthesis of $X_nMg(OR)_2$–n by preparing an alkanol adduct of a magnesium halide, reacting the product of this step with metallic magnesium, and drying the product. The compositions are then evaluated for as catalysts of olefin polymerization. The main disadvantage of this process is the usage of magnesium halides and large amount of alcohols.

U.S. Pat. No. 4,820,672 of Lithium Corporation of America describes the process for producing magnesium halide alcohol complex by reacting in an ether free hydrocarbon reaction medium, magnesium metal, dialkyl magnesium, alkyl magnesium halide, alkyl magnesium alkoxide, magnesium dialkoxide and alkoxy magnesium halide with an anhydrous hydrogen halide in the presence of chloro substituted alcohol. Further this complex is used for synthesis of ZN catalyst. The main disadvantage of this process is a large number of steps are involved for magnesium halide alcohol synthesis and further the usage of hydrogen halide which is difficult to handle. This patent contains no information on the activity of the ZN catalyst synthesized thereof.

U.S. Pat. No. 4,820,879 further describes the process where alkoxy magnesium halides are formed by reacting pre activated magnesium with alcohol at higher temperatures and then treating it with hydrogen halides. Here also usage and handling of hydrogen halide is quite troublesome.

U.S. Pat. No. 5,081,320 of Akzo NV describes the synthesis of alkoxymagnesium halides from secondary alcohol containing alkyl branching on the alpha carbon atom which is soluble in inert hydrocarbon. The process involves heating inert hydrocarbon solvent, secondary alcohol and ethanol with magnesium halide ($MgCl_2$) to dissolve the magnesium halide. Magnesium metal is then added along with additional solvent to prepare a soluble alkoxymagnesium halide. One disadvantage of this process is one need to prepare soluble magnesium alkoxide in order to further react the magnesium metal.

U.S. Pat. No. 5,108,972 discloses the process of synthesis of alkoxymagnesium halide using non Grignard route where they react magnesium halide and magnesium alkoxide in excess of alcohol. Further magnesium source can also be added which is generated through dialkylmagnesium in hydrocarbon. Main disadvantage of this process is usage of expensive raw materials and large number of steps. The patent describes the process of synthesizing the magnesium compounds only.

U.S. Pat. No. 5,414,158 of Witco GmbH describes synthesis of alkoxymagnesium halides in an inert hydrocarbon by reacting preactivated magnesium with small quantities of magnesium alkyl, with almost equimolar mixture of an alkyl halide and an alkanol. The obtained product is in excess of 90%. In this process first magnesium needs to be activated with magnesium alkyl at high temperature and then addition is carried out dropwise to the alkylhalide and alkanol mixture. One disadvantage of this process is requirement of expensive magnesium alkyl for activation which is also difficult to handle and further the extra addition of alkanol after the reaction to reduce viscosity.

EP1273595 of Borealis describes the process for synthesis of catalyst by reacting dialkylmagnesium with monohydric alcohol followed by dicarboxylic acid dihalide and chlorinated hydrocarbons. After washing and isolation of this product, it is further treated with titanium compound for the formation of ZN catalyst which shows activity for propylene polymerization. The main disadvantage of this process is usage of expensive dialkylmagnesium and its handling. This patent is mainly focused on the usage of emulsion stabilizer for controlling the particle size and shape.

U.S. Pat. No. 7,135,531 of BASF discloses the process for the synthesis of spherical catalyst which essentially contains titanium, internal donor and a support made from a magnesium compound, an alcohol, ether, a surfactant, and an alkyl silicate. The magnesium compound mainly magnesium dichloride is dissolve in alcohol at higher temperature and then treated with ether at lower temperature followed by addition of emulsifier at still lower temperature. This is then treated with silicate and titanium compound and final catalyst is ready after washing and drying. The main disadvantage of this process is higher alcohol content and expensive raw materials.

US2009/0306315 of SABIC discloses the process for preparing a polymerization catalyst which is synthesized by reacting $Mg(OR^1)_xCl_{2-x}$, which is obtained by reacting a Grignard compound with an alkoxy or aryloxy silane compound, with electron donor in the presence of inert dispersant to give an intermediate reaction product which is then treated with titanium halide to give the final catalyst which shows activity for olefin polymerization. This process has main disadvantage that its involves large number of steps which mainly consists of, first solubilizing the magnesium compound and then solidifying before making final catalyst.

SUMMARY OF INVENTION

Accordingly the present invention provides a liquid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.1-99.8:0.1-99.8:0.1-99.8, and a process for preparing the same. The said process comprises contacting a magnesium source with an organohalide and alcohol in a solvent to form the liquid organomagnesium precursor.

The present invention also provides a process for preparation of a catalyst composition, said process in a reaction system comprises:

(a) contacting titanium compound represented by $M(OR''')_p X_{4-p}$, where M is a transition metal and selected from Ti, V, Zr, and Hf; X is a halogen atom; R''' is a hydrocarbon group and p is an integer having value equal or less than 4 and where M is preferably titanium, with the solution of organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.1-99.8:0.1-99.8:0.1-99.8, to obtain a resulting solution and the contact temperature of organomagnesium precursor and titanium compound is between about −50° C. and about 150° C., and preferably between about −30° C. and about 120° C.;

(b) adding an internal donor either to the organomagnesium precursor component or to the titanium component and the contact time of the said component with the internal electron donor is either immediate or at least 1 minutes to 60 minutes at contact temperature of between about −50° C. and about 100° C., and preferably between about −30° C. and about 90° C.;

(c) treating the resulting solution obtained in the step (a) with a solution comprising neat titanium component or titanium component in a solvent and recovering a solid titanium catalyst component and maintaining the same at a temperature value in the range of 90 to 120° C. for about 10 to 60 minutes; and (d) optionally repeating step (c) for a predetermined number of times and then washed sufficiently with inert solvent at temperature 20° C. to 90° C. to obtain a solid catalysts composition.

The present invention also provides a process for preparation of a Ziegler-Natta catalyst system, said process comprises contacting the said catalyst composition with at least one cocatalyst, and at least one external electron donor to obtain a Ziegler-Natta catalyst system.

The present invention also provides a method of polymerizing and/or copolymerizing olefins, said method comprising the step of contacting an olefin having C2 to C20 carbon atoms under a polymerizing condition with the said Ziegler-Natta catalyst system.

DETAILED DESCRIPTION OF INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The present invention relates to a process for the preparing a precursor for a catalyst system. Further the invention discloses a process for preparing the catalyst system using the precursor and its use thereof. The catalyst system is used for the polymerization of olefins. The present invention discloses a single step process for preparing the precursor.

According to the present invention there is provided a process of preparation of an organometallic compound which is used as a precursor for the preparation of the catalyst system for the polymerization of olefins.

The process according to the present invention comprises preparing the organometallic compound such as organomagnesium compound in-situ by reacting magnesium with organohalide in presence of solvent with an alcohol. The obtained liquid organomagnesium compound was contacted with metal compound M; wherein M can be selected from group including, but not limited to Ti, V, Zr, Hf and internal electron donors to provide the catalyst system. This catalyst system comprising of the said component have high activity for olefin polymerization with good hydrogen response and high stereospecificity.

In an embodiment of the present invention, there is provided a process for preparing liquid organomagnesium based precursor which is stable and synthesized through single step. In addition, the liquid organomagnesium compound is used without further purification for making olefin polymerization catalyst which shows improved activity.

The present invention is the single step process through which liquid organomagnesium compound is synthesized using magnesium, organohalide and alcohol in the solvent resulting in the formation of stable organomagnesium compound. The liquid organomagnesium compound is then used as a precursor for the synthesis of Ziegler-Natta catalysts which is prepared through precipitation, physical blending of solid mixtures, in-situ formation of halogenating agents and so forth. According to the present invention the precursor synthesis is achieved with reduced alcohol content without any further purification and the precursors are quite stable. The whole mixture can be used for catalyst synthesis. The resulting catalyst exhibits high activity for olefin polymerization with good hydrogen response.

Accordingly the present invention provides a liquid organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.1-99.8:0.1-99.8:0.1-99.8, and a process for preparing the same. The said process comprises contacting a magnesium source with an organohalide and alcohol in a solvent to form a liquid organomagnesium precursor.

In one of the preferred embodiment, a liquid organomagnesium precursor having formula {Mg(OR')X}.a{MgX$_2$}.b{Mg(OR')$_2$}.c{R'OH} can be prepared as shown in below scheme 1:

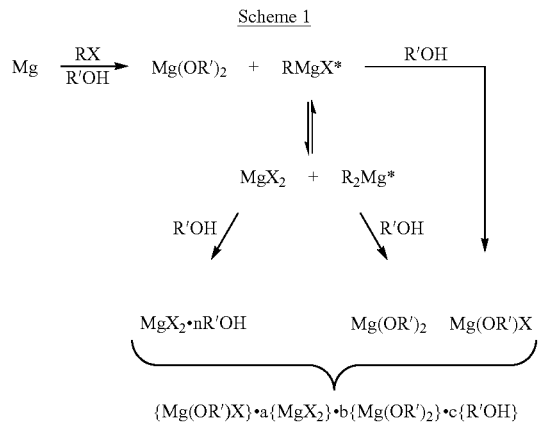

Scheme 1 wherein,
Mg—Magnesium Metal
RX—Alkyl Halide
RMgX—Grignard Reagent
*Intermediates
R'OH—Alcohol
Ratio of a:b:c is in range of 0.1-99.8:0.1-99.8:0.1-99.8;
R and R' is selected from a hydrocarbon groups;
X is halogen selected from Cl, Br or I; and
n is an integer having value 1-10

Further, the invention provides a process of polymerizing and/or copolymerizing the olefin using the catalyst produced through the process mentioned in the invention.

The present invention provides liquid organomagnesium compounds as precursor for Ziegler-Natta catalyst system and method of synthesis of organomagnesium compounds and the catalyst component. The catalyst components synthesized from organomagnesium compounds are able to polymerize olefins. The present liquid organomagnesium precursor based catalyst system has high activity, good hydrogen response, high selectivity and better comonomer distribution.

According to the present invention, the process of preparing liquid organomagnesium compound involves contacting magnesium source with organohalide compound, alcohol and suitable solvent for specified time and at particular temperature. In an embodiment of the invention, the magnesium source used in the present invention includes, but not limited to magnesium metal in form of powder, ribbon, turnings, wire, granules, block, lumps, chips; dialkylmagnesium compounds such as dimethylmagnesium, diethylmagnesium, diisopropylmagnesium, dibutylmagnesium, dihexylmagnesium, dioctylmagnesium, ethylbutylmagnesium, and butyloctylmagnesium; alkyl/aryl magnesium halides such as methylmagnesium chloride, ethylmagnesium chloride, isopropylmagnesium chloride, isobutylmagnesium chloride, tert-butylmagnesium chloride, benzylmagnesium chloride, methylmagnesium bromide, ethylmagnesium bromide, isopropylmagnesium bromide, isobutylmagnesium bromide, tert-butylmagnesium bromide, hexylmagnesium bromide, benzylmagnesium bromide, methylmagnesium iodide, ethylmagnesium iodide, isopropylmagnesium iodide, isobutylmagnesium iodide, tert-butylmagnesium iodide, and benzylmagnesium iodide. These magnesium compounds may be in the liquid or solid state. In a preferred embodiment of the invention, the magnesium compound is preferably magnesium metal.

In an embodiment of the present invention, the organohalide which is contacted with magnesium compound, includes, but not limited to alkyl halides either branched or linear such as methyl chloride, ethyl chloride, propyl chloride, isopropyl chloride, dichloromethane, chloroform, carbon tetrachloride, 1,1-dichloropropane, 1,2-dichloropropane, 1,3-dichloropropane, 2,3-dichloropropane, n-butyl chloride, iso-butyl chloride, 1,4-dichlorobutane, tert-butylchloride, amylchloride, tert-amylchloride, 2-chloropentane, 3-chloropentane, 1,5-dichloropentane, 1-chloro-8-iodoctane, 1-chloro-6-cyanohexane, cyclopentylchloride, cyclohexylchloride, chlorinated dodecane, chlorinated tetradecane, chlorinated eicosane, chlorinated pentacosane, chlorinated triacontane, iso-octylchloride, 5-chloro-5-methyl decane, 9-chloro-9-ethyl-6-methyl eiscosane; benzylic halides, such as benzyl chloride and α,α' dichloro xylene; other halogenated alkyl benzene and the like as well as the corresponding bromine, fluorine and iodine substituted hydrocarbons. These organohalides may be used alone or in the form of mixture thereof. In an embodiment of the invention, the organohalide is preferably butyl chloride or benzyl chloride or their mixture thereof.

In an embodiment of the present invention, the alcohol contacted includes, but not limited to, for example, aliphatic alcohols such as methanol, ethanol, propanol, n-butanol, iso-butanol, t-butanol, n-pentanol, iso-pentanol, n-hexanol, 2-methylpentanol, 2-ethylbutanol, n-heptanol, n-octanol, 2-ethylhexanol, decanol and dodecanol; alicyclic alcohols such as cyclohexanol and methylcyclohexanol; aromatic alcohols such as benzyl alcohol and methylbenzyl alcohol; aliphatic alcohols containing an alkoxy group, such as ethyl glycol, butyl glycol; diols such as catechol, ethylene glycol, 1,3-propanediol, 1,4-butanediol, 1,5-pentanediol, 1,8-octanediol, 1,2-propanediol, 1,2-butanediol, 2,3-butanediol 1,3-butanediol, 1,2-pentanediol, p-menthane-3,8-diol, 2-methyl-2,4-pentanediol. These alcohols may be used alone or in the form of mixture thereof.

In an embodiment of the present invention, the solvent in which all the components are contacted may be polar or non polar aromatic or aliphatic in nature examples not limiting to benzene, decane, kerosene, ethyl benzene, chlorobenzene, dichlorobenzene, toluene, o-chlorotoluene, xylene, dichloromethane, chloroform, cyclohexane and the like and their mixtures thereof. The solvent preferably is toluene or chlorobenzene and their mixture.

In an embodiment of the present invention, the components may be added in any order preferably, magnesium followed by solvent, organohalide and alcohol.

The quantity of organohalide depends upon the quantity of magnesium compound used. According to the preferred embodiment, the magnesium source is reacted with the said organohalide in a molar ratio of between 1:20 to 1:0.2, preferably between about 1:10 to 1:0.5, more preferably, between 1:4 to 1:0.5. In another embodiment, the magnesium source along with organohalide is reacted with the said alcohol in a molar ratio of between 1:20 to 1:0.2, preferably between about 1:10 to 1:0.5, more preferably, between 1:4 to 1:0.5.

According to another embodiment of the present invention, formation of homogeneous solution of magnesium component in alcohol is desirable. For attaining this, the magnesium compound, organohalide, alcohol compound in the solvent are contacted at temperature preferably between about 0° C. and about 150° C., and more preferably between about 10° C. and about 120° C. According to an embodiment of the invention, the contact time is for about 0.5 to 12 h.

In an embodiment, reaction promoters like iodine, the organohalides, inorganic halides such as CuCl, $MnCl_2$, AgCl, nitrogen halides like N-halide succinimides, trihaloisocynauric acid N-halophthalimide and hydrantoin compounds, ethers like diethyl ether, dibutyl ether, t-butyl methyl ether, tetrahydrofuran, dioxanes etc can be used in the process of the present invention.

In accordance with the present invention, there is provided a process for making soluble magnesium based precursor for olefin polymerization catalyst in which the source of magnesium is reacted with organohalide in desired solvent having alcohol. The resulting mixture of organomagnesium may contain alkoxy magnesium halide, magnesium dihalide and dialkoxy magnesium compounds which further form adducts with alcohol that are soluble in desired solvent.

The present invention provides the process of preparation of organomagnesium compound which involves contacting magnesium compound with organohalide compound, alcohol and suitable solvent for particular time and at particular temperature. In an embodiment, the resulting solution is stable as the solution shows no precipitation even after couple of months and the precursor is always in solvent hence is protected from external influences.

In an embodiment, the resulting organomagnesium solution can be used as such as precursor for making olefin polymerization catalyst system without any further purification or isolation. In another embodiment, the resulting organomagnesium solution can be precipitated before being used as precursor for making olefin polymerization catalyst system.

In another embodiment of the present invention, the precipitation can be done using polar as well as non polar organic liquid component examples not limiting to linear, branched, aromatic, cyclic, ring substituted, halide substituted alkanes and the like and their mixtures thereof. The organomagnesium solution can also be partially concentrated before precipitation. Also, the precipitation can be carried out either by addition of organomagnesium solution to the organic liquid component or vice versa. In another embodiment, the precipitated solid can be either used directly or in solution form for catalyst synthesis where in the solvent used for dissolving solid can be from the following group but not limited to polar and non polar aliphatic and/or aromatic hydrocarbons.

The present invention provides a catalyst composition. The catalyst composition includes combination of a magnesium moiety, other metal moiety and an internal donor. The magnesium moiety includes the organomagnesium compound. The other metal moiety can be a main group metal or a transition metal, or a transition metal of IIIB-VIIIB element. In an embodiment, the transition metal is selected from group including but not limited to Ti, V, Zr, and Hf, preferably, Ti.

In one of the embodiment the present invention provides a process for preparation of a catalyst composition, said process in a reaction system comprises:

(a) contacting titanium compound represented by $M(OR')_p X_{4-p}$, where M is a transition metal and is selected from a group comprising of Ti, V, Zr, and Hf, preferably Ti, X is a halogen atom; R''' is a hydrocarbon group and p is an integer having value equal or less than 4 with the solution of organomagnesium precursor having formula {Mg(OR') X}.a{MgX$_2$}.b{Mg(OR')$_2$}.c{R'OH}, wherein R' is selected from a hydrocarbon group, X is selected from a halide group, and a:b:c is in range of 0.1-99.8:0.1-99.8:0.1-99.8, to obtain a resulting solution and the contact temperature of organomagnesium precursor and titanium compound is between about −50° C. and about 150° C., and preferably between about −30° C. and about 120° C.;

(b) adding an internal donor either to the organomagnesium precursor component or to the titanium component and the contact time of the said component with the internal electron donor is either immediate or at least 1 minutes to 60 minutes at contact temperature of between about −50° C. and about 100° C., and preferably between about −30° C. and about 90° C.;

(c) treating the resulting solution obtained in the step (a) with a solution comprising neat titanium component or titanium component in a solvent and recovering a solid titanium catalyst component and maintaining the same at a temperature value in the range of 90 to 120° C. for about 10 to 60 minutes; and (d) optionally repeating step (c) for a predetermined number of times and then washed sufficiently with inert solvent at temperature 20° C. to 90° C. to obtain a solid catalysts composition.

In yet another embodiment of the present invention, the transition metal compound represented by $M(OR''')_p X_{4-p}$ is selected from a group comprising of transition metal tetrahalide, alkoxy transition metal trihalide/aryloxy transition metal trihalide, dialkoxy transition metal dihalide, trialkoxy transition metal monohalide, tetraalkoxy transition metal, and mixtures thereof;

wherein:

(a) the transition metal tetrahalide is selected from a group comprising of titanium tetrachloride, titanium tetrabromide and titanium tetraiodide and the likes for V, Zr and Hf;

(b) alkoxy transition metal trihalide/aryloxy transition metal trihalide is selected from a group comprising of methoxytitanium trichloride, ethoxytitanium trichloride, butoxytitanium trichloride and phenoxytitanium trichloride and the likes for V, Zr and Hf;

(c) dialkoxy transition metal dihalide is diethoxy titanium dichloride and the likes for V, Zr and Hf;

(d) trialkoxy transition metal monohalide is triethoxy titanium chloride and the likes for V, Zr and Hf; and (e) tetraalkoxy transition metal is selected from a group comprising of tetrabutoxy titanium and tetraethoxy titanium and the likes for V, Zr and Hf.

The present invention also provides a process for preparation of a Ziegler-Natta catalyst system, said process comprises contacting the said catalyst composition with at least one cocatalyst, and at least one external electron donor to obtain a Ziegler-Natta catalyst system.

The present invention also provides a method of polymerizing and/or copolymerizing olefins, said method comprising the step of contacting an olefin having C2 to C20 carbon atoms under a polymerizing condition with the said Ziegler-Natta catalyst system.

The present invention provides the catalyst composition which comprises combination of magnesium moiety, titanium moiety and an internal donor. The magnesium moiety includes the organomagnesium compound. In an embodiment, the invention provides the method of synthesis of olefin polymerizing catalyst, comprising of reacting the organomagnesium compound with liquid titanium compound which comprises tetravalent titanium compound represented as $Ti(OR)_p X_{4-p}$ wherein X can be halogen selected from Cl or Br or I, R is a hydrocarbon group and p is an integer varying from 0-4. Specific examples of the titanium compound include, but not limited to titanium tetrahalides such as titanium tetrachloride, titanium tetrabromide, titanium tetraiodide; alkoxytitanium trihalide/aryloxytitanium trihalide such as methoxytitanium trichloride, ethoxytitanium trichloride, butoxytitanium trichloride, phenoxytitanium trichloride; dialkoxy titanium dihalides such as diethoxy titanium dichloride; trialkoxytitanium monohalide such as triethoxy titanium chloride; and tetraalkoxytitanium such as tetrabutoxy titanium, tetraethoxy titanium, and mixtures thereof, with titanium tetrachloride being preferred. These titanium compounds may be used alone or in the form of mixture thereof.

According to the present invention, the magnesium moiety includes the organomagnesium compound. In an embodiment, the contact of organomagnesium compound with titanium compound can be either neat or in solvent which can be chlorinated or non chlorinated aromatic or aliphatic in nature. Examples of solvents include but not limiting to benzene, decane, kerosene, ethyl benzene, chlorobenzene, dichlorobenzene, toluene, o-chlorotoluene, xylene, dichloromethane, chloroform, cyclohexane and the like, comprising from 5 to 95 volume percent.

In an embodiment of the present invention, either the titanium compound is added to the organomagnesium compound or vice-verse, preferably, organomagnesium compound is added to titanium compound.

In another embodiment, this addition is either one shot or drop wise. In another embodiment, the contact temperature of organomagnesium and titanium compound is preferably between about −50° C. and about 150° C., and more preferably between about −30° C. and about 120° C.

The liquid titanium compound helps in the formation of amorphous $MgCl_2$ as it acts as halogenating agent as well as is dispersed and supported on the catalyst surface. Moreover, the removal of alcohol from the solution, results in the precipitation of the solid component, having especially desired surface properties and particle shape. More important, the particles are uniform in shape. In an embodiment, the titanium compound is added in amounts ranging from usually about at least 1 to 200 moles, preferably, 3 to 200 moles and more preferably, 5 mole to 100 moles, with respect to one mole of magnesium.

While preparing the catalyst composition, magnesium component is contacted with the titanium component along with the internal donor to get the solid titanium component. In another embodiment, magnesium and titanium component can be made to come in contact with the internal electron donor.

In another embodiment, the solid titanium catalyst component is made by contacting a magnesium compound and a titanium compound in the presence of an internal electron donor compound.

Further in an embodiment, the solid titanium catalyst component is made by forming a magnesium based catalyst support optionally with the titanium compound and optionally with the internal electron donor compound, and contacting the magnesium based catalyst support with the titanium compound and the internal electron donor compound.

The present invention provides the catalyst composition which includes combination of magnesium moiety, titanium moiety and an internal donor. The magnesium moiety includes the organomagnesium compound. In an embodiment, internal electron donor is selected from phthalates, benzoates, diethers, succinates, malonates, carbonates, and combinations thereof. Specific examples include, but are not limited to di-n-butyl phthalate, di-i-butyl phthalate, di-i-octyl phthalate, di-n-octyl phthalate, di-n-nonyl phthalate, di-2-ethylhexyl phthalate, methyl benzoate, ethyl benzoate, propyl benzoate, phenyl benzoate, cyclohexyl benzoate, methyl toluate, ethyl toluate, p-ethoxy ethyl benzoate, p-isopropoxy ethyl benzoate, diethyl succinate, di-propyl succinate, diisopropyl succinate, dibutyl succinate, diisobutyl succinate, diethyl malonate, diethyl ethylmalonate, diethyl propyl malonate, diethyl isopropylmalonate, diethyl butylmalonate, diethyl 1,2-cyclohexanedicarboxylate, di-2-ethylhexyl 1,2-cyclohexanedicarboxylate, di-2-isononyl 1,2-cyclohexanedicarboxylate, methyl anisate, ethyl anisate and diether compounds such as 9,9-bis(methoxymethyl)fluorene, 2-isopropyl-2-isopentyl-1,3-dimethoxypropane, 2,2-diisobutyl-1,3-dimethoxypropane, 2,2-diisopentyl-1,3-dimethoxypropane, 2-isopropyl-2-cyclohexyl-1,3-dimethoxypropane, preferably di-iso-butyl phthalate.

The "internal electron donor" is a compound that is added during the formation of catalyst composition where it is acting as Lewis base i.e. donating the electron pairs to the metal present in the catalyst composition. The internal electron donor stabilizes the primary crystallites of magnesium dihalide which is generated in-situ. Apart from this, the internal donor also being better Lewis base have preferred coordination with the higher acidity coordination sites on magnesium dihalide matrix which in turn avoid the coordination of titanium and hence prevents the formation of inactive sites. They also increase the activity of low active sites. This in all enhances the catalyst stereoselectivity. All internal electron donor compounds commonly used in the art can be used in the present invention. In another embodiment, the internal electron donor is used in an amount of from 0 to 1 moles, preferably from 0.01 to 0.5 moles, with respect to one mole of magnesium.

In an embodiment of the present invention, the addition of internal donor is either to the organomagnesium compound or to the titanium component, preferably to organomagnesium compound. The contact temperature of internal donor depends upon to which component it is being added. In an embodiment, the contact time of the desired component with the internal electron donor is either immediate or at least 1 minutes to 60 minutes at contact temperature of preferably between about −50° C. and about 100° C., and more preferably between about −30° C. and about 90° C.

Typically, the contact procedure for titanium and magnesium component is slowly with dropwise addition or continuous flow or single shot at desired temperature and then heated to activate the reaction between both the components.

In a preferred embodiment of this invention, this reaction system is gradually heated to the temperature effective to carry out the reaction, preferably about −50° C. and about 150° C., and more preferably about −30° C. and about 120° C., and heating is instigated at a rate of 0.1 to 10.0° C./minute, or at a rate of 1 to 5.0° C./minute. The resultant is the solid catalyst component in the solvent comprising of magnesium, titanium and halogen components.

The procedure of contacting the titanium component may be repeated one, two, three or more times as desired. In an embodiment, the resulting solid material recovered from the mixture can be contacted one or more times with the mixture of liquid titanium component in solvent for at least 10 minutes up to 60 minutes, at temperature from about 25° C. to about 150° C., preferably from about 30° C. to about 110° C.

The resulting solid catalyst composition/component comprising of magnesium, titanium, halogen, alcohol and the internal electron donor can be separated from the reaction mixture either by filtration or decantation and finally washed with inert solvent to remove the unreacted titanium component and other side products. Usually, the resultant solid material is washed one or more times with inert solvent which is typically a hydrocarbon including, not limiting to aliphatic hydrocarbon like isopentane, isooctane, heptanes, hexane, pentane or isohexane.

In an embodiment, the resulting solid mixture is washed one or more times with inert hydrocarbon based solvent preferably, hexane at temperature from about 20° C. to about 100° C., preferably from about 25° C. to about 90° C. The solid catalyst then can be separated and dried or slurried in a hydrocarbon specifically heavy hydrocarbon such as mineral oil for further storage or use.

In an embodiment, the catalyst composition includes from about 2.0 wt % to 20 wt % of internal electron donor, titanium is from about 0.5 wt % to 10.0 wt % and magnesium is from about 10 wt % to 20 wt %.

The present invention provides the catalyst system for polymerization of olefins. In an embodiment, the method of polymerization process is provided where the catalyst system is contacted with olefin under polymerization conditions. The catalyst system includes catalyst composition, organoaluminum compounds and external electron donors. The catalyst composition includes combination of magnesium moiety, titanium moiety and an internal donor. The magnesium moiety includes the organomagnesium compound.

The catalyst system includes catalyst composition, cocatalyst and external electron donors. The catalyst composition includes combination of magnesium moiety, titanium moiety and an internal donor. The magnesium moiety includes the organomagnesium compound or organomagnesium precursor. The cocatalyst may include hydrides, organoaluminum, lithium, zinc, tin, cadmium, beryllium, magnesium, and combinations thereof. In an embodiment, the cocatalyst is organoaluminum compounds.

The olefins according to the present invention includes from C2-C20. The ratio of titanium (from catalyst composition):aluminum (from organoaluminum compound):external donor can be from 1:5-2000:0-250, preferably in the range from 1:25-1000:25-100.

The present invention provides the catalyst system. The catalyst system includes catalyst component, organoaluminum compounds and external electron donors. In an embodiment, the organoaluminum compounds include, not limiting, alkylaluminums such as trialkylaluminum such as preferably triethylaluminum, triisopropylaluminum, triisobutylaluminum, tri-n-butylaluminum, tri-n-hexylaluminum, tri-n-octylaluminum; trialkenylaluminums such as triisoprenyl aluminum; dialkylaluminum halides such as diethylaluminum chloride, dibutylaluminum chloride, diisobutylaluminum chloride and diethyl aluminum bromide; alkylaluminum sesquihalides such as ethylaluminum sesquichloride, butylaluminum sesquichloride and ethylaluminum sesquibromide; dialkylaluminum hydrides such as diethylaluminum hydride and dibutylaluminum hydride; partially hydrogenated alkylaluminum such as ethylaluminum dihydride and propylaluminum dihydride and aluminoxane such as methylaluminoxane, isobutylaluminoxane, tetraethylaluminoxane and tetraisobutylaluminoxane; diethylaluminum ethoxide and combination thereof. The mole ratio of aluminum to titanium is from about 5:1 to about 2000:1 or from about 10:1 to about 1500:1, or from about 25:1 to about 500:1.

The present invention provides the catalyst system. The catalyst system includes catalyst component, organoaluminum compounds and external electron donors. The external electron donors are organosilicon compounds, diethers and alkoxy benzoates. The external electron donor for olefin polymerization when added to the catalytic system as a part of cocatalyst retains the stereospecificity of the active sites, convert non-stereospecific sites to stereospecific sites, poisons the non-stereospecific sites and also controls the molecular weight distributions while retaining high performance with respect to catalytic activity. In an embodiment, the external electron donors which are generally organosilicon compounds includes but are not limited to trimethylmethoxysilane, trimethylethoxysilane, dimethyldimethoxysilane, dimethyldiethoxysilane, diisopropyldimethoxysilane, diisobutyldimethoxysilane, t-butylmethyldimethoxysilane, t-butylmethyldiethoxysilane, t-amylmethyldiethoxysilane, dicyclopentyldimethoxysilane, diphenyldimethoxysilane, phenylmethyldimethoxysilane, diphenyldiethoxysilane, bis-o-tolydimethoxysilane, bis-m-tolydimethoxysilane, bis-p-tolydimethoxysilane, bis-p-tolydiethoxysilane, bisethylphenyldimethoxysilane, dicyclohexyldimethoxysilane, cyclohexylmethyldimethoxysilane, cyclohexylmethyldiethoxysilane, ethyltrimethoxysilane, ethyltriethoxysilane, vinyltrimethoxysilane, methyltrimethoxysilane, n-propyltriethoxysilane, decyltrimethoxysilane, decyltriethoxysilane, phenyltrimethoxysilane, gamma-chloropropyltrimethoxysilane, methyltriethoxysilane, ethyltriethoxysilane, vinyltriethoxysilane, t-butyltriethoxysilane, n-butyltriethoxysilane, isobutyltriethoxysilane, phenyltriethoxysilane, gamma-aminopropyltriethoxysilane, cholotriethoxysilane, ethyltriisopropoxysilane, vinyltirbutoxysilane, cyclohexyltrimethoxysilane, cyclohexyltriethoxysilane, 2-norbornanetrimethoxysilane, 2-norbornanetriethoxysilane, 2-norbornanemethyldimethoxysilane, ethyl silicate, butyl silicate, trimethylphenoxysilane, and methyltriallyloxysilane, cyclopropyltrimethoxysilane, cyclobutyltrimethoxysilane, cyclopentyltrimethoxysilane, 2-methylcyclopentyltrimethoxysilane, 2,3-dimethylcyclopentyltrimethoxysilane, 2,5-dimethylcyclopentyltrimethoxysilane, cyclopentyltriethoxysilane, cyclopentenyltrimethoxysilane, 3-cyclopentenyltrimethoxysilane, 2,4-cyclopentadienyltrimethoxysilane, indenyltrimethoxysilane and fluorenyltrimethoxysilane; dialkoxysilanes such as dicyclopentyldimethoxysilane, bis(2-methylcyclopentyl)dimethoxysilane, bis(3-tertiary butylcyclopentyl)dimethoxysilane, bis(2,3-dimethylcyclopentyl)dimethoxysilane, bis(2,5-dimethylcyclopentyl)dimethoxysilane, dicyclopentyldiethoxysilane, dicyclobutyldiethoxysilane, cyclopropylcyclobutyldiethoxysilane, dicyclopentenyldimethoxysilane, di(3-cyclopentenyl)dimethoxysilane, bis(2,5-dimethyl-3-cyclopentenyl)dimethoxysilane, di-2,4-cyclopentadienyl)dimethoxysilane, bis(2,5-dimethyl-2,4-cyclopentadienyl)dimethoxysilane, bis(1-methyl-1-cyclopentylethyl)dimethoxysilane, cyclopentylcyclopentenyldimethoxysilane, cyclopentylcyclopentadienyldimethoxysilane, diindenyldimethoxysilane, bis(1,3-dimethyl-2-indenyl)dimethoxysilane, cyclopentadienylindenyldimethoxysilane, difluorenyldimethoxysilane, cyclopentylfluorenyldimethoxysilane and indenylfluorenyldimethoxysilane; monoalkoxysilanes such as tricyclopentylmethoxysilane, tricyclopentenylmethoxysilane, tricyclopentadienylmethoxysilane, tricyclopentylethoxysilane, dicyclopentylmethylmethoxysilane, dicyclopentylethylmethoxysilane, dicyclopentylmethylethoxysilane, cyclopentyldimethylmethoxysilane, cyclopentyldiethylmethoxysilane, cyclopentyldimethylethoxysilane, bis(2,5-dimethylcyclopentyl)cyclopentylmethoxysilane, dicyclopentylcyclopentenylmethoxysilane, dicyclopentylcyclopentenadienylmethoxysilane, diindenylcyclopentylmethoxysilane and ethylenebis-cyclopentyldimethoxysilane; aminosilanes such as aminopropyltriethoxysilane, n-(3-triethoxysilylpropyl)amine, bis [(3-triethoxysilyl)propyl]amine, aminopropyltrimethoxysilane, aminopropylmethyldiethoxysilane, hexanediaminopropyltrimethoxysilane.

Further in an embodiment, the external electron donor, other than organosilicon compounds include, but not limited to amine, diether, esters, carboxylate, ketone, amide, phosphine, carbamate, phosphate, sulfonate, sulfone and/or sulphoxide.

The external electron donor is used in such an amount to give a molar ratio of organoaluminum compound to the said external donor from about 0.1 to 500, preferably from 1 to 300.

In the present invention, the polymerization of olefins is carried out in the presence of the catalyst system described above. The catalyst system is contacted with olefin under polymerization conditions to produce desired polymer products. The polymerization process can be carried out such as slurry polymerization using as diluents which is an inert hydrocarbon solvent, or bulk polymerization using the liquid monomer as a reaction medium and in gas-phase operating in one or more fluidized or mechanically agitated bed reactors. In an embodiment, polymerization is carried out as such. In another embodiment, the copolymerization is carried out using at least two polymerization zones.

The catalyst of the invention can be used in the polymerization of the above-defined olefin $CH_2$=CHR, the examples of said olefin include ethylene, propylene, 1-butene, 4-methyl-1-pentene, 1-hexene, and 1-octene.

In particular, said catalyst can be used to produce, such as, the following products: high-density polyethylene (HDPE, having a density higher than 0.940 g/cm3), which includes ethylene homopolymer and copolymer of ethylene and α-olefins having 3 to 12 carbon atoms; linear low-density polyethylene (LLDPE, having a density lower than 0.940 g/cm3), and very low density and ultra low density polyethylene (VLDPE and ULDPE, having a density lower than 0.920 g/cm3, and as low as 0.880 g/cm3), consisting of the copolymer of ethylene and one or more α-olefins having 3 to 12 carbon atoms, wherein the molar content of the unit derived from ethylene is higher than 80%; elastomeric copolymer of ethylene and propylene, and elastomeric terpolymers of ethylene, propylene and 1-butene as well as diolefins at a small ratio, wherein the weight content of the unit derived from ethylene is between about 30% and 70%; isotactic polypropylene and crystalline copolymer of propylene and ethylene and/or other α-olefins, wherein the content of the unit derived from propylene is higher than 85% by weight (random copolymer); impact propylene polymer, which are produced by sequential polymerization of propylene and the mixture of propylene and ethylene, with the content of ethylene being up to 40% by weight; copolymer of propylene and 1-butene, containing a great amount, such as from 10 to 40 percent by weight, of unit derived from 1-butene. It is especially significant that the propylene polymers produced by using the catalysts of the invention show very broad molecule weight distribution (MWD) and have very high isotactic index.

In an embodiment of the invention, the polymerization is carried out at a temperature from 20 to 120° C., preferably from 40 to 80° C. When the polymerization is carried out in gas phase, operation pressure is usually in the range of from 5 to 100 bar, preferably from 10 to 50 bar. The operation pressure in bulk polymerization is usually in the range of from 10 to 150 bar, preferably from 15 to 50 bar. The operation pressure in slurry polymerization is usually in the range of from 1 to 10 bar, preferably from 2 to 7 bar. Hydrogen can be used to control the molecular weight of polymers.

In the present invention, the polymerization of olefins is carried out in the presence of the catalyst system described above. The described catalyst can be directly added to the reactor for polymerization or can be prepolymerized i.e. catalyst is subjected to a polymerization at lower conversion extent before being added to polymerization reactor. Prepolymerization can be performed with olefins preferably ethylene and/or propylene where the conversion is controlled in the range from 0.2 to 500 gram polymer per gram catalyst.

In the present invention, the polymerization of olefins in presence of the described catalyst system leads to the formation of polyolefins having xylene soluble (XS) value from about 0.2% to about 15%. In another embodiment, polyolefins is having xylene soluble (XS) value from about 2% to about 8%. Here XS refers to the weight percent of polymer that get dissolves into hot xylene generally for measuring the tacticity index such as highly isotactic polymer will have low XS % value i.e. higher crystallinity, whereas low isotactic polymer will have high XS % value.

The present invention provides the catalyst system. The catalysts system when polymerizes olefins provides polyolefins having melt flow indexes (MFI) from about 0.1 to about 100 which is measured according to ASTM standard D1238. In an embodiment, polyolefins having MFI from about 5 to about 30 are produced.

The present invention provides the catalyst system. The catalyst system when used for polymerizing olefins provides polyolefins having bulk densities (BD) of at least about 0.3 cc/g.

The following non-limiting examples illustrate in details about the invention. However, they are, not intended to be limiting the scope of present invention in any way.

EXAMPLE 1

Preparation of Organomagnesium Compound

In 500 ml glass reactor maintained at 25° C., calculated amount of magnesium (powder or turnings) were weighed and added into the reactor followed by addition of calculated amount of organohalide followed by alcohol in toluene. This mixture was stirred and gradually heated to 90° C.±3. After the activation of the reaction, the mixture was allowed to be maintained at same temperature for 6 h. The resulting solution was slightly viscose in nature. The organomagnesium compounds synthesized by the above procedure have been tabulated in Table 1.

TABLE 1

| Precursor | Mg Ratio | Benzyl chloride Ratio | BuCl Ratio | Alcohol Ratio | Solvent | Alcohol | Mg (wt %) | Remark |
|---|---|---|---|---|---|---|---|---|
| MGP#1 | 1 | 0 | 2 | 1 | Toluene | EHA | 1.1 | |
| MGP#2 | 1 | 4.3 | 0 | 1 | Toluene | EHA | 1.5 | |

TABLE 1-continued

| Precursor | Mg Ratio | Benzyl chloride Ratio | BuCl Ratio | Alcohol Ratio | Solvent | Alcohol | Mg (wt %) | Remark |
|---|---|---|---|---|---|---|---|---|
| MGP#3 | 1 | 0 | 2 | 1 | Toluene | EHA | — | |
| MGP#4 | 1 | 0 | 4 | 1 | Toluene | EHA | 0.7 | |
| MGP#5 | 1 | 0 | 2 | 1 | Toluene | EHA | 1.0 | |
| MGP#6 | 1 | 1.2 | 0 | 1.1 | Toluene | EHA | 1.2 | |
| MGP#7 | 1 | 0.7 | 0 | 0.7 | Toluene | EHA | 0.9 | |
| MGP#8 | 1 | 0.7 | 0 | 0.7 | Toluene | EHA | 0.8 | |
| MGP#9 | 2 | 1.5 | 0 | 1 | Toluene | EHA | 0.9 | |
| MGP#10 | 1 | 0 | 2 | 1 | Toluene | EHA | 0.2 | |
| MGP#11 | 1 | 0 | 2 | 1 | Toluene | EHA | 0.8 | |
| MGP#12 | 1.5 | 1.2 | 0 | 1 | Toluene | EHA | 0.6 | |
| MGP#13 | 1 | 0 | 2 | 1 | Toluene | EHA | 0.4 | |
| MGP#14 | 1 | 0 | 2 | 1 | Toluene | EHA | 0.5 | |
| MGP#15 | 1 | 0 | 1.1 | 1 | Toluene | EHA | 0.4 | |
| MGP#16 | 1.5 | 2 | 0 | 1 | Toluene | EHA | 0.4 | |
| MGP#17 | 1 | 1.1 | 0 | 1 | Toluene | EHA | 1.0 | |
| MGP#18 | 1 | 0 | 2 | 1 | Toluene | EHA | 0.1 | |
| MGP#19 | 1.2 | 1.1 | 0 | 1 | Toluene | EHA | 1.0 | |
| MGP#20 | 1 | 0 | 2 | 1 | Toluene | EHA | — | |
| MGP#21 | 1.0 | 0.8 | 0 | 0.8 | Toluene | EHA | 0.7 | |
| MGP#22 | 1 | 0.5 | 0 | 1 | Heptane | EHA | — | |
| MGP#23 | 1 | 0 | 1.4 | 1 | heptane | EHA | 0.4 | |
| MGP#24 | 1 | 0 | 1 | 1 | Toluene | EHA | 0.6 | |
| MGP#26 | 1 | 0 | 1.1 | 1 | Toluene | EHA | 0.1 | Dibutylether (0.2 equi) |
| MGP#28 | 1 | 0 | 1 | 0.8 | Toluene | EHA | 0.6 | |
| MGP#29 | 1 | 0 | 1.1 | 1 | Toluene | EHA | 0.8 | Dibutylether (1 equiv.) |
| MGP#30 | 1 | 0 | 1 | 1 | Toluene | EHA | 0.6 | Dibutylether (1 equiv.) |
| MGP#32 | 1 | 0 | 1.5 | 1 | Toluene | EHA | 1.3 | Diethylether (0.25 equiv.) |
| MGP#35 | 1 | 0 | 1 | 2 | Toluene | EHA | 0.4 | |
| MGP#36 | 1 | 0 | 1 | 3 | Toluene | EHA | 0.2 | |
| MGP#39 | 1 | 1.2 | 0 | 1.2 | Toluene | EHA | 1.2 | |
| MGP#40 | 1 | 1.2 | 0 | 1.2 | Toluene | EHA | 1.5 | |
| MGP#44 | 1 | 0 | 2 | 1 | Toluene | EHA | 0.5 | |
| MGP#46 | 1.0 | 1.2 | 0 | 1.2 | Toluene | Benzyl alcohol | 0.7 | |
| MGP#49 | 1 | 1.2 | 0 | 1.2 | Toluene | Isobutanol | 1.1 | |
| MGP#50 | 1 | 1.2 | 0 | 1.2 | Toluene | EHA | 1.2 | |
| MGP#52 | 1 | 1.2 | 0 | 1.2 | Toluene | Catechol | — | No rxn |
| MGP#54 | 1 | 1.2 | 0 | 1.2 | Toluene | Isobutanol | 1.2 | |
| MGP#55 | 1 | 1.2 | 0 | 1.2 | Toluene | Cresol | 1.2 | |
| MGP#107 | 1 | 1.1 | 0 | 2.0 | Toluene | EHA | 1.8 | |
| MGP#108 | 1 | 1 | 0 | 2.0 | Toluene | EHA | 1.6 | |
| MGP#110 | 1 | 1.05 | 0 | 2.0 | Toluene | EHA | 1.7 | |
| MGP#113 | 1 | 1.1 | 0 | 1.8 | Chlorobenzene | EHA | 1.5 | |
| MGP#121 | 1 | 1.1 | 0 | 2.0 | Chlorobenzene | EHA | 1.8 | |

EHA = 2-ethyl-1-hexanol

The table 1 shows the synthesis of organomagnesium compound used as precursor with various alcohols and organohalides in different solvents.

EXAMPLE 2

Preparation of the Catalyst Component/Composition

To 60 ml of TiCl$_4$ solution maintained at desired temperature, added 100 ml of the organomagnesium precursor along with internal donor over a period of 10 min and stirred. After the system has attained the desired temperature, the resultant solution was maintained at the same temperature for 15 min. The resultant solution was clear orange in color. Gradually the reaction temperature was increased to 110° C. and maintained for 0.5 h. After settling and decantation, the suspended solid was again treated with 60 ml TiCl$_4$ and 60 ml chlorobenzene and after temperature reached 110° C., the mixture was maintained under stirring for 15 minutes. The above step was again repeated. After the reaction was finished, the solid was decanted and washed sufficiently with hexane at 70° C., respectively and further dried under hot nitrogen till freely flowing. The solid catalysts composition synthesized by the above procedure has been tabulated in Table 2.

TABLE 2

| Catalyst | Precursor | Precursor & TiCl$_4$ contact temperature ° C. | Internal donor addition ° C. | Remark | Ti (wt %) | Mg (wt %) | Donor (wt %) |
|---|---|---|---|---|---|---|---|
| ZN#90 | MGP#1 | 30 | 70 | | 4.6 | 15.8 | 25.9 |
| ZN#91 | MGP#2 | 0 | 0 | | 1.6 | 13.6 | 17.2 |

TABLE 2-continued

| Catalyst | Precursor | Precursor & TiCl$_4$ contact temperature ° C. | Internal donor addition ° C. | Remark | Ti (wt %) | Mg (wt %) | Donor (wt %) |
|---|---|---|---|---|---|---|---|
| ZN#92 | MGP#1 | 30 | 30 | | 5.3 | 13.3 | 23.4 |
| ZN#94 | MGP#6 | 40 | 90 | | 4.1 | 11.8 | 26.6 |
| ZN#97 | MGP#6 | 40 | 90 | Reduced ID amt | 4.6 | 16.8 | 16.7 |
| ZN#98 | MGP#17 | 40 | 90 | | 3.7 | 17.2 | 14.7 |
| ZN#99 | MGP#29 | 40 | 90 | | 2.1 | 16.9 | 19.0 |
| ZN#100 | MGP#30 | 40 | 90 | | 1.2 | 17.8 | 22.1 |
| ZN#101 | MGP#17 | 40 | 90 | Dibutyl ether added | 2.0 | 15.9 | 26.3 |
| ZN#106 | MGP#46 | 40 | 90 | | 4.4 | 13.1 | 11.1 |
| ZN#108 | MGP#49 | 40 | 90 | | 3.4 | 17.2 | 13.3 |
| ZN#112 | MGP#40 | −5 | −5 | | 3.4 | 15.8 | 14.1 |
| ZN#113 | MGP#49 | −5 | −5 | | 3.5 | 17.1 | 11.4 |
| ZN#114 | MGP#40 | −5 | −5 | | 3.3 | 15.7 | 14.9 |
| ZN#115 | MGP#49 | −5 | −5 | | 2.7 | 18.3 | 14.6 |
| ZN#117 | MGP#50 | −5 | −5 | | 4.1 | 10.6 | — |
| ZN#118 | MGP#50 | −5 | −5 | | 5.6 | 12.8 | — |
| ZN#140 | MGP#50 | 15 | 15 | titanation@ 90° C. | 2.5 | 13.3 | — |
| ZN#144 | MGP#50 | −5 | −5 | Reduced TiCl$_4$ amount | 3.0 | 16.6 | — |
| ZN#259 | MGP#107 | −20 | −20 | | 3.1 | 16.1 | 17.5 |
| ZN#262 | MGP#121 | −20 | −20 | | 3.9 | 20.3 | 11.9 |

Table 2 provides the details of catalyst synthesis process at various contact time of precursor with titanium component. The catalyst composition especially with respect to titanium incorporation remains stable irrespective of the variation in synthesis methodology.

EXAMPLE 3

Slurry Polymerization of Propylene

Propylene polymerization was carried out in 1 L buchi reactor which was previously conditioned under nitrogen. The reactor was charged with 250 ml of dry hexane containing solution of 10 wt % triethylaluminum followed by 100 ml of dry hexane containing 10 wt % solution of triethylaluminum, 5 wt % solution of cyclohexy methyl dimethoxysilane and weighed amount of catalyst. The reactor was pressurized with hydrogen to 60 ml then charged with 71 psi of propylene under stirring at 750 rpm. The reactor was heated to and then held at 70° C. for 2 hour. In the end, the reactor was vented and the polymer was recovered at ambient conditions.

Catalyst performance and polymer properties has been tabulated in Table 3

TABLE 3

| CATALYST | | POLYMERIZATION | | | | POLYMER ANALYSIS | | |
|---|---|---|---|---|---|---|---|---|
| Cat No | Cat wt (mg) | Al/Ti ratio | H2 ml | Al/Do ratio | Activity kgPP/ gcat | MFI @2.16 kg | XS wt % | T$_{MP}$ ° C. |
| ZN#90 | 34.1 | 250 | 60 | 20 | 3.7 | 14.6 | 2.2 | 163.4 |
| | 13.8 | 250 | 60 | 20 | 4.7 | 9.6 | 1.5 | 160.8 |
| | 15.3 | 250 | 20 | 20 | 6.5 | 8.2 | 1.2 | 160.8 |
| ZN#97 | 14.3 | 250 | 20 | 20 | 8.4 | 33.3 | 2.9 | 160.5 |
| ZN#98 | 14.6 | 250 | 20 | 20 | 6.8 | 5.5 | 1.9 | 161.0 |
| | 14.5 | 250 | 10 | 20 | 6.9 | 4.8 | 2.0 | 161.2 |
| ZN#99 | 30.3 | 250 | 10 | 20 | 0.1 | 4.8 | 2 | 159.9 |
| ZN#101 | 25.3 | 250 | 10 | 20 | 0 | — | — | 159.6 |
| ZN#108 | 15.3 | 250 | 10 | 20 | 8.0 | 4.5 | 1.4 | 159.4 |
| ZN#112 | 15.2 | 250 | 10 | 20 | 9.5 | 6.7 | 1.8 | 159.0 |
| | 10.1 | 250 | 10 | 20 | 12.5 | 3.4 | 2.0 | 163.0 |
| | 13.4 | 500 | 10 | 20 | 8.7 | 5.6 | 2.5 | 163.4 |
| | 13.8 | 500 | 10 | 20 | 8.9 | 4.8 | 2.5 | 160.8 |
| | 12.8 | 250 | 10 | 20 | 8.6 | 5.1 | 1.8 | 160.5 |
| | 10.0 | 500 | 10 | 20 NPTMS | 8.6 | 3.3 | 8.7 | 161.0 |
| | 10.2 | 500 | 10 | 20 NPTES | 8.3 | 8.9 | 5.4 | 161.2 |
| | 10.3 | 500 | 10 | 20 DPDMS | 10.8 | 2.2 | 7.1 | 163.4 |
| ZN#113 | 15.1 | 250 | 10 | 20 | 4.3 | 4.5 | 4.3 | 160.8 |
| ZN#114 | 10.3 | 250 | 10 | 20 | 12.3 | 3.7 | 2.5 | 161.1 |
| ZN#115 | 14.8 | 500 | 10 | 20 | 6.7 | 4.7 | 1.8 | 160.2 |
| ZN#118 | 14.6 | 500 | 10 | 20 | 7.3 | 3.5 | 4.0 | 161.2 |
| ZN#140 | 10.2 | 500 | 10 | 20 | 4.4 | 1.6 | 3.6 | 160.6 |
| ZN#144 | 10.2 | 500 | 10 | 20 | 10.1 | 2.5 | 1.6 | 162.0 |

NPTMS = n-propyl trimethoxy silane
NPTES = n-propyl triethoxy silane
DPDMS = diphenyl dimethoxy silane Table 3 shows the catalyst efficacy for propylene polymerization showing good hydrogen response and external donor response.

What is claimed Is:

1. A process for preparation of a liquid organomagnesium precursor having formula {Mg(OR')X}.a{MgX$_2$}. b{Mg(OR')$_2$}.c{R'OH} wherein R' is selected from a hydrocarbon group, X is selected from a halide group, and a:b:c is in range of 0.1-99.8:0.1-99.8:0.1-99.8, said process comprising:
   contacting a magnesium source with an organohalide and an alcohol in a solvent to form the organomagnesium precursor,
   wherein the liquid organomagnesium precursor is synthesized through a single step.

2. The process as claimed in claim 1, wherein the magnesium source is selected from the group consisting of magnesium metal, dialkyl magnesium, alkyl/aryl magnesium halides and mixtures thereof; wherein:
  (a) the magnesium metal is in form of powder, ribbon, turnings, wire, granules, block, lumps, chips;
  (b) the dialkylmagnesium compounds is selected from the group consisting of dimethylmagnesium, diethylmagnesium, diisopropylmagnesium, dibutylmagnesium, dihexylmagnesium, dioctylmagnesium, ethylbutylmagnesium, and butyloctylmagnesium; and
  (c) alkyl/aryl magnesium halides is selected from the group consisting of methylmagnesium chloride, ethylmagnesium chloride, isopropylmagnesium chloride, isobutylmagnesium chloride, tert-butylmagnesium chloride, benzylmagnesium chloride, methylmagnesium bromide, ethylmagnesium bromide, isopropylmagnesium bromide, isobutylmagnesium bromide, tert-butylmagnesium bromide, hexylmagnesium bromide, benzylmagnesium bromide, methylmagnesium iodide, ethylmagnesium iodide, isopropylmagnesium iodide, isobutylmagnesium iodide, tert-butylmagnesium iodide, and benzylmagnesium iodide.

3. The process as claimed in claim 1, wherein the magnesium source is magnesium metal.

4. The process as claimed in claim 1, wherein the organohalide is selected from the group consisting of alkyl halides either branched or linear, halogenated alkyl benzene/benzylic halides having an alkyl radical contains from about 10 to 15 carbon atoms and mixtures thereof; wherein:
  (a) the alkyl halides is selected from the group consisting of methyl chloride, ethyl chloride, propyl chloride, isopropyl chloride, dichloromethane, chloroform, carbon tetrachloride, 1,1-dichloropropane, 1,2-dichloropropane, 1,3-dichloropropane, 2,3-dichloropropane, n-butyl chloride, iso-butyl chloride, 1,4-dichlorobutane, tert-butylchloride, amylchloride, tert-amyl chloride, 2-chloropentane, 3-chloropentane, 1,5-dichloropentane, 1-chloro-8-iodoctane, 1-chloro-6-cyanohexane, cyclopentylchloride, cyclohexylchloride, chlorinated dodecane, chlorinated tetradecane, chlorinated eicosane, chlorinated pentacosane, chlorinated triacontane, iso-octylchloride, 5-chloro-5-methyl decane, 9-chloro-9-ethyl-6-methyl eiscosane; and
  (b) the halogenated alkyl benzene/benzylic halides is selected from the group consisting of benzyl chloride and α,α' dichloro xylene.

5. The process as claimed in claim 1, wherein the organohalide is butyl chloride or benzyl chloride or their mixture.

6. The process as claimed in claim 1, wherein the alcohol is selected from the group consisting of aliphatic alcohols, alicyclic alcohols, aromatic alcohols, aliphatic alcohols containing an alkoxy group, diols and mixture thereof; wherein:
  (a) the aliphatic alcohols is selected from the group consisting of methanol, ethanol, propanol, n-butanol, iso-butanol, t-butanol, n-pentanol, iso-pentanol, n-hexanol, 2-methylpentanol, 2-ethylbutanol, n-heptanol, n-octanol, 2-ethylhexanol, decanol and dodecanol,
  (b) the alicyclic alcohols is selected from the group consisting of cyclohexanol and methylcyclohexanol,
  (c) the aromatic alcohols is selected from the group consisting of benzyl alcohol and methylbenzyl alcohol,
  (d) the aliphatic alcohols containing an alkoxy group is selected from the group consisting of ethyl glycol and butyl glycol;
  (e) the diols is selected from the group consisting of catechol, ethylene glycol, 1,3-propanediol, 1,4-butanediol, 1,5-pentanediol, 1,8-octanediol, 1,2-propanediol, 1,2-butanediol, 2,3-butanediol, 1,3-butanediol, 1,2-pentanediol, p-menthane-3,8-diol, and 2-methyl-2,4-pentanediol.

7. The process as claimed in claim 1, wherein the solvent is selected from the group consisting of a polar aromatic solvent, non-polar aromatic solvent, polar aliphatic solvent and a non-polar aliphatic solvent.

8. The process as claimed in claim 1, wherein the solvent is selected from the group consisting of benzene, decane, kerosene, ethyl benzene, chlorobenzene, dichlorobenzene, toluene, o-chlorotoluene, xylene, dichloromethane, chloroform, cyclohexane and the like and their mixtures thereof.

9. The process as claimed in claim 1, wherein the solvent is toluene or chlorobenzene or their mixture.

10. The process as claimed in claim 1, wherein the magnesium source is reacted with the organohalide in a molar ratio of between 1:20 to 1:0.2.

11. The process as claimed in claim 1, wherein the magnesium source along with organohalide is reacted with the alcohol in a molar ratio of between 1:20 to 1:0.2.

12. The process as claimed in claim 1, wherein the magnesium source, organohalide, and alcohol compound in the solvent are contacted at temperature between about 0° C. and about 150° C., and the contact time is for about 0.5 to 12 h for the formation of a homogeneous solution of magnesium component in alcohol.

13. The process as claimed in claim 1, further comprises a reaction promoter, which is selected from the group consisting of iodine, the organohalides, inorganic halides, nitrogen halides, ethers and mixture thereof; wherein:
  (a) the inorganic halide is selected from the group consisting of CuCl, $MnCl_2$, and AgCl;
  (b) the nitrogen halide is selected from the group consisting of N-halide succinimide, trihaloisocynauric acid, N-halophthalimide and hydrantoin compound; and
  (c) the ether is selected from the group consisting of diethyl ether, dibutyl ether, t-butyl methyl ether, tetrahydrofuran, and dioxane.

14. The process as claimed in claim 1, wherein the organomagnesium precursor is stable.

15. The process as claimed in claim 1, wherein the organomagnesium precursor is used for making olefin polymerization catalyst system without any further purification or isolation.

16. An organomagnesium precursor having formula $\{Mg(OR')X\}.a\{MgX_2\}.b\{Mg(OR')_2\}.c\{R'OH\}$ wherein R' is selected from a hydrocarbon group, X is selected from a halide group, and a:b:c is in range of 0.1-99.8:0.1-99.8:0.1-99.8.

17. A process for preparation of a catalyst composition, said process in a reaction system comprising:
  (a) contacting titanium compound represented by $M(OR''')_pX_{4-p}$, where M is a transition metal and is Ti; X is a halogen atom; R''' is a hydrocarbon group and p is an integer having value equal or less than 4 with a solution of organomagnesium precursor having formula $\{Mg(OR')X\}.a\{MgX_2\}.b\{Mg(OR')_2\}.c\{R'OH\}$, wherein R' is selected from a hydrocarbon group, X is selected from a halide group, and a:b:c is in range of 0.1-99.8:0.1-99.8:0.1-99.8, to obtain a resulting solution and the contact temperature of the organomagnesium precursor and the titanium compound is between about −50° C. and about 150° C.
  (b) adding an internal donor before the step (a) either to the organomagnesium precursor or to the titanium compound and the contact time of the organomagnesium precursor or the titanium compound with the internal electron donor is either immediate or at least 1 minutes to 60 minutes at contact temperature of between about −50° C. and about 100° C.;

(c) treating the resulting solution obtained in the step (a) with a solution comprising neat titanium component or titanium component in a solvent and recovering a solid titanium catalyst component and maintaining the same at a temperature value in the range of 90 to 120° C. for about 10 to 60 minutes; and (d) optionally repeating step (c) for a predetermined number of times and then washed sufficiently with inert solvent at temperature 20° C. to 90° C. to obtain a solid catalysts composition.

18. The process as claimed in claim 17, wherein the titanium compound represented by $M(OR''')_pX_{4-p}$ is selected from the group consisting of transition metal tetrahalide, alkoxy transition metal trihalide/aryloxy transition metal trihalide, dialkoxy transition metal dihalide, trialkoxy transition metal monohalide, tetraalkoxy transition metal, and mixtures thereof; wherein:

(a) the transition metal tetrahalide is selected from the group consisting of titanium tetrachloride, titanium tetrabromide and titanium tetraiodide;

(b) alkoxy transition metal trihalide/aryloxy transition metal trihalide is selected from the group consisting of methoxytitanium trichloride, ethoxytitanium trichloride, butoxytitanium trichloride and phenoxytitanium trichloride;

(c) dialkoxy transition metal dihalide is diethoxy titanium dichloride;

(d) trialkoxy transition metal monohalide is triethoxy titanium chloride; and (e) tetraalkoxy transition metal is selected from the group consisting of tetrabutoxy titanium and tetraethoxy titanium.

19. The process as claimed in claim 17, wherein the internal electron donor used is selected from the group consisting of phthalates, benzoates, succinates, malonates, carbonates, diethers and combinations thereof wherein:

(a) the phthalate is selected from the group consisting of di-n-butyl phthalate, di-i-butyl phthalate, di-i-octyl phthalate, di-n-octyl phthalate, di-n-nonyl phthalate, di-2-ethylhexyl phthalate;

(b) the benzoate is selected from the group consisting of methyl benzoate, ethyl benzoate, propyl benzoate, phenyl benzoate, cyclohexyl benzoate, methyl toluate, ethyl toluate, p-ethoxy ethyl benzoate and p-isopropoxy ethyl benzoate;

(c) the succinate is selected from the group consisting of diethyl succinate, di-propyl succinate, diisopropyl succinate, dibutyl succinate and diisobutyl succinate, (d) the malonate is selected from the group consisting of diethyl malonate, diethyl ethylmalonate, diethyl propyl malonate, diethyl isopropylmalonate, diethyl butylmalonate;

(e) the carbonate compound is selected from the group consisting of diethyl 1,2-cyclohexanedicarboxylate, di-2-ethylhexyl 1,2-cyclohexanedicarboxylate, di-2-isononyl 1,2-cyclohexanedicarboxylate, methyl anisate and ethyl anisate; and (f) the diether compound is selected from the group consisting of 9,9-bi s(methoxymethyl)fluorene, 2-i sopropyl-24 sopentyl-1,3-dimethoxypropane, 2,2-diisobutyl-1,3 -dimethoxypropane, 2,2-diisopentyl-1,3 -dimethoxypropane and 2-isopropyl-2-cyclohexyl-1,3-dimethoxypropane.

20. The process as claimed in claim 17, wherein step (a) the organomagnesium precursor contact with titanium compound either neat or in solvent.

21. The process as claimed in claim 20, wherein the solvent is selected from the group consisting of chlorinated aromatic hydrocarbon, non chlorinated aromatic hydrocarbon chlorinated aliphatic hydrocarbon, non chlorinated aliphatic hydrocarbon and combination thereof.

22. The process as claimed in claim 20, wherein the solvent is comprising from 5 to 95 volume percent and is selected from the group consisting of benzene, decane, kerosene, ethyl benzene, chlorobenzene, dichlorobenzene, toluene, o-chlorotoluene, xylene, dichloromethane, chloroform, cyclohexane and combination thereof.

23. The process as claimed in claim 17, wherein in step (a) either the titanium compound is added to the organomagnesium compound or vice-verse.

24. The process as claimed in claim 17, wherein step (a) comprising adding organomagnesium compound with titanium compound.

25. The process as claimed in claim 17, wherein step (b) comprising adding organomagnesium precursor with internal donor.

26. The process as claimed in claim 17, wherein in step (b) the internal electron donor is used in an amount of from 0 to 1 mole with respect to one mole of magnesium.

27. The process as claimed in claim 17, wherein the reaction system is gradually heated to the temperature effective to carry out the reaction, about −50° C. and about 150° C., and heating is instigated at a rate of 0.1 to 10.0° C./minute to obtain the solid catalyst component in the solvent comprising magnesium, titanium and halogen components.

* * * * *